US008663240B2

(12) United States Patent
Kling et al.

(10) Patent No.: US 8,663,240 B2
(45) Date of Patent: Mar. 4, 2014

(54) HYBRID HAIR REMOVAL DEVICE

(75) Inventors: Björn Kling, Glashütten (DE); Bernhard Sikora, Kelkheim (DE); Bernd Pfeiffer, Schwalbach (DE)

(73) Assignee: Braun GmbH, Kronberg (DE)

( * ) Notice: Subject to any disclaimer, the term of this patent is extended or adjusted under 35 U.S.C. 154(b) by 138 days.

(21) Appl. No.: 12/984,027

(22) Filed: Jan. 4, 2011

(65) Prior Publication Data

US 2011/0094106 A1 Apr. 28, 2011

Related U.S. Application Data

(63) Continuation of application No. PCT/EP2009/004821, filed on Jul. 3, 2009.

(30) Foreign Application Priority Data

Jul. 15, 2008 (EP) .................................... 08012724
Apr. 21, 2009 (EP) .................................... 09005577

(51) Int. Cl.
*A61B 17/50* (2006.01)

(52) U.S. Cl.
USPC .......................................................... 606/133

(58) Field of Classification Search
USPC ............ 606/36, 43, 133, 144; 30/34.2, 34.05, 30/34.1; 451/71, 82, 83, 85, 86, 102, 103, 451/104; 452/71, 82, 83, 85, 86, 102, 103, 452/104
See application file for complete search history.

(56) References Cited

U.S. PATENT DOCUMENTS

| | | | | |
|---|---|---|---|---|
| 3,252,217 | A | 5/1966 | Werft | |
| 5,980,452 | A * | 11/1999 | Garenfeld et al. | 600/133 |
| 6,052,905 | A | 4/2000 | Branchinelli et al. | |
| 6,308,413 | B1 | 10/2001 | Westerhof et al. | |
| 8,109,001 | B2 | 2/2012 | Royle et al. | |
| 2002/0161380 | A1 | 10/2002 | Saitou et al. | |
| 2007/0220756 | A1 * | 9/2007 | Royle et al. | 30/42 |
| 2008/0216322 | A1 | 9/2008 | Molema et al. | |
| 2008/0301947 | A1 | 12/2008 | Dorber et al. | |
| 2010/0139097 | A1 | 6/2010 | Perez-Lopez et al. | |
| 2011/0005082 | A1 | 1/2011 | Fischer et al. | |

FOREIGN PATENT DOCUMENTS

| | | |
|---|---|---|
| DE | 2002/1185 U1 | 3/2001 |
| EP | 2 220 958 A1 | 8/2010 |
| JP | 48-082487 | 7/1973 |
| JP | 53-013589 | 2/1978 |

(Continued)

OTHER PUBLICATIONS

European Search Report dated Sep. 9, 2009, 2 pages.

*Primary Examiner* — Thomas McEvoy

(74) *Attorney, Agent, or Firm* — Jeffrey V Bamber; Kim W Zerby

(57) ABSTRACT

The present invention is concerned with a hybrid hair removal device that comprises an electrical hair removal device having a body that is intended for being gripped by a user's hand and a head that is intended for contact with a user's skin during regular operation, and an attachment that comprises a handle structure that detachably envelopes at least a part of the outer surface of the body and a skin treatment unit mounted at the handle structure. Such a hybrid hair removal device allows easily detaching the attachment from the hair removal device. The invention is also concerned with such an attachment.

9 Claims, 3 Drawing Sheets

(56) References Cited

FOREIGN PATENT DOCUMENTS

| | | | |
|---|---|---|---|
| JP | 60-066781 | A | 9/1983 |
| JP | 01-209093 | A | 8/1989 |
| WO | WO-2007/008520 | A | 1/2007 |
| WO | WO 2008/092625 | A1 | 8/2008 |
| WO | WO 2010/009179 | A1 | 1/2010 |

* cited by examiner

HYBRID HAIR REMOVAL DEVICE

CROSS REFERENCE TO RELATED APPLICATIONS

This application is a continuation of prior co-pending International Application No. PCT/EP2009/004821 filed Jul. 3, 2009, designating the United States.

FIELD OF THE INVENTION

The present invention is concerned with a hybrid hair removal device and it is specifically concerned with a hybrid hair removal device that comprises an electrical hair removal device and a further skin treatment unit.

BACKGROUND OF THE INVENTION

International patent application WO 2008/092625 A1 describes a hybrid hair removal device that comprises an electrical hair removal unit (an electrical long hair trimmer) that is combined with a further skin treatment unit, namely a safety razor. The safety razor is movably mounted to the back of the electrical trimmer

SUMMARY OF THE INVENTION

It is desirable to provide a hybrid hair removal device that is improved over the known devices or that at least is an alternative to the known devices.

Such a hybrid hair removal device is given in accordance with claim 1. The dependent claims describe further embodiments.

The hybrid hair removal device as proposed comprises an electrical hair removal device that has a body that is intended to be gripped by a user's hand and a head that is intended to get into contact with the users skin during regular operation. The hybrid hair removal device further comprises an attachment that has a handle structure and a skin treatment unit. The handle structure of the attachment is detachably enveloping at least part of the body of the electrical hair removal device. In particular, the handle structure is clamped around the body. The handle structure may therefore have an inner side that is concavely shaped (designed somewhat smaller than the outer shape of the body) so that it can be clamped around the body of the electrical hair removal device. The skin treatment unit can specifically be a unit that e.g. massages the skin, applies an application material—e.g. a lotion—to the skin, or that is arranged to remove hairs from the skin. Hence, the attachment adds a further function to the electrical hair removal device. A hybrid hair removal device as proposed can hence comprise an electrical hair removal device that the user may buy independently from the attachment. As the attachment is only enveloping at least a part of the body of the electrical hair removal device, the electrical hair removal device does not need to be modified to accommodate the attachment. In the attached state, the skin treatment unit can be arranged at the attachment such that the head of the electrical hair removal unit and the skin treatment unit simultaneously contact the skin when the hybrid hair removal device is pressed against the user's skin. The handle structure may in particular be elongated so that the handle to structure can be conveniently be gripped by a user's hand in the detached state and hence allows for individual use of the attachment in the detached state.

In an embodiment, the skin treatment unit comprises at least a razor blade (a blade cartridge as is commonly known from safety razors may be arranged so as to comprise the razor blade). The skin treatment unit may then be arranged so that the head of the electrical hair removal device lies in front of the skin treatment unit with respect to the use direction that is defined by the razor blade. In such a combination, the electrical hair removal device removes the hairs growing on the skin and the razor blade shave off all remaining hairs or hair stubbles during the same stroke. Hence, a clean and smooth skin feeling results.

In another embodiment, the skin treatment unit is detachably connected to the handle structure. This allows removing the skin treatment unit, e.g. to replace it with a fresh skin treatment unit (e.g. a fresh safety razor blade cartridge with sharp blades or a fresh applicator to apply a lubricant to the skin etc.). In a refinement of this embodiment, the handle structure comprises a release mechanism(which may comprise a release button as is commonly known from release mechanisms of safety razors) to detach the skin treatment unit from the handle structure.

In yet another embodiment, the skin treatment unit is floatingly mounted at the handle structure. This allows that in operation the skin treatment unit and the head of the electrical hair removal device can simultaneously contact the skin even if the user does not hold the hybrid hair removal device at the advised angle with respect to the skin The skin treatment unit may further be arranged so as to pivot around a pivot axis as is generally known in the art of safety razors, which pivotable mounting would further enhance the ability to adapt to the skin surface independent of the angle with which the device is held with respect to the skin or independent of the skin surface topology, which may be uneven in some areas (e.g. in the arm pit of around the knee). In a refinement of this embodiment, the attachment comprises a fixation mechanism to fix the skin treatment unit with respect to the handle structure (i.e. to disable the floating mounting). This specifically is sensible if the attachment is to be used individually in the detached state.

In even another embodiment, the handle structure is enveloping around two sides of the body of the electrical hair removal device. This improves fixation of the attachment to the electrical hair removal device but still allows for easily removing the attachment from the body of the electrical hair removal device. Fixation may be accomplished by clamping forces (i.e. the enveloping inner side of the handle structure is designed to be slightly smaller than the body of the electrical hair removal device) and/or by adhesion forces (i.e. the material of the inner side of the handle structure may specifically adhere to the outer surface of the body as would rubber adhere to a polished plastic surface). In yet a different embodiment, the handle structure envelopes three sides of the body (i.e. it envelopes the body in a shoe-like manner In a further embodiment, the handle structure envelopes four sides of the body, e.g. the handle structure comprises flexible parts that can be bend outwards while the attachment is slipped over three sides of the body and those flexible parts will finally also envelope the body in the attached state. For enhanced fixation of the handle structure to the body, the handle structure may comprise openings or recesses for form-fit enclosure of respective projections of the body.

In general, it is explained for sake of clarity that the head of the electrical hair removal device is not enveloped (or covered) by the handle structure of the attachment to allow for simultaneous hair removal and skin treatment.

In a further embodiment, the handle structure comprises a first connector structure that mates in the attached state with a second connector structure realized at the body. The first and second connector structures may in particular be designed as detachable force-fit or snap-fit connector structures.

In an even further embodiment, the handle structure of the attachment has an outer side that is intended for being gripped by a user's hand. The surface of the outer side is at least partially textured. A texture enhances the grip of the handle structure, specifically when the hybrid hair removal device is intended for use in a wet environment. Hence, the outer side of the body of the electrical hair removal device can be made smooth and shiny, while the outer side of the handle structure is made at least partially textured. The texture may comprise rip-like structures, burl-like structures, any other elevations, openings in the outer surface, depressions, recesses, or indentations. The texture is in particular a macroscopic texture and the structure may have a minimal lateral dimension along the outer surface of 0.5 mm to optimally enhance the grip of the outer surface.

In a specific embodiment, the electrical hair removal device is an epilator device for plucking to hairs from the skin. In another specific embodiment, the electrical hair removal device is a dry shaver. The electrical hair removal device may also be realized as a long hair trimmer The invention is also concerned with an attachment for an electrical hair removal device. The attachment is in accordance with the attachment as described as part of the hybrid hair removal device.

BRIEF DESCRIPTION OF THE DRAWINGS

The invention will be further described and elucidated by discussion of an exemplary embodiment and by reference to figures. In the figures

DETAILED DESCRIPTION OF THE INVENTION

Figure 1A:
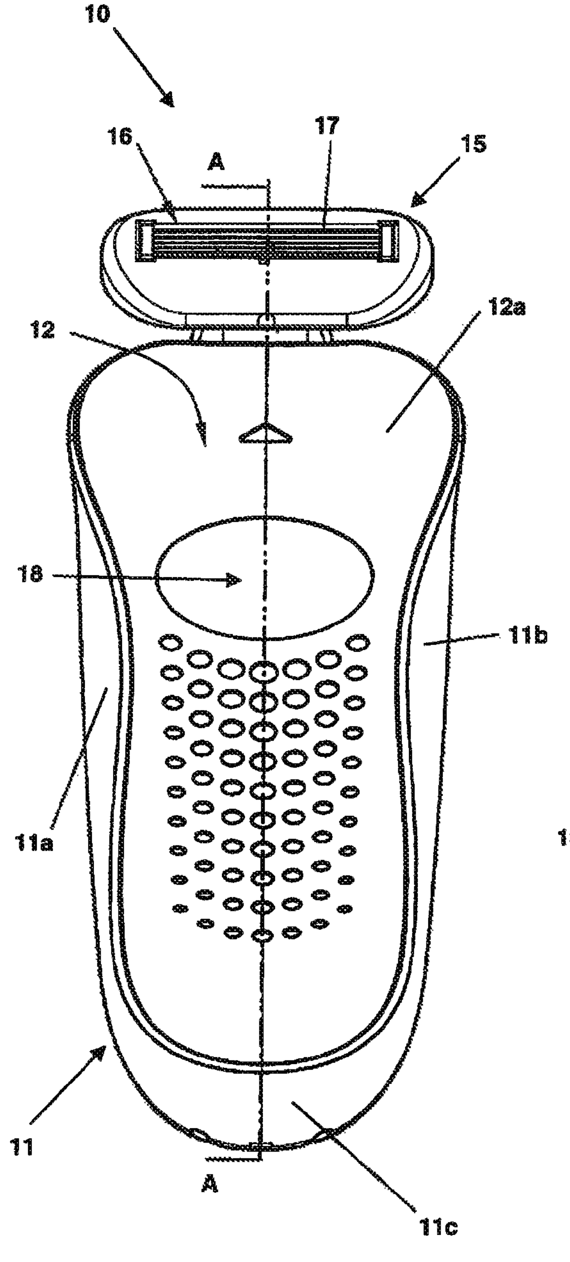
FIG. 1A is a view onto the front of an exemplary attachment as proposed.
Figure 3:
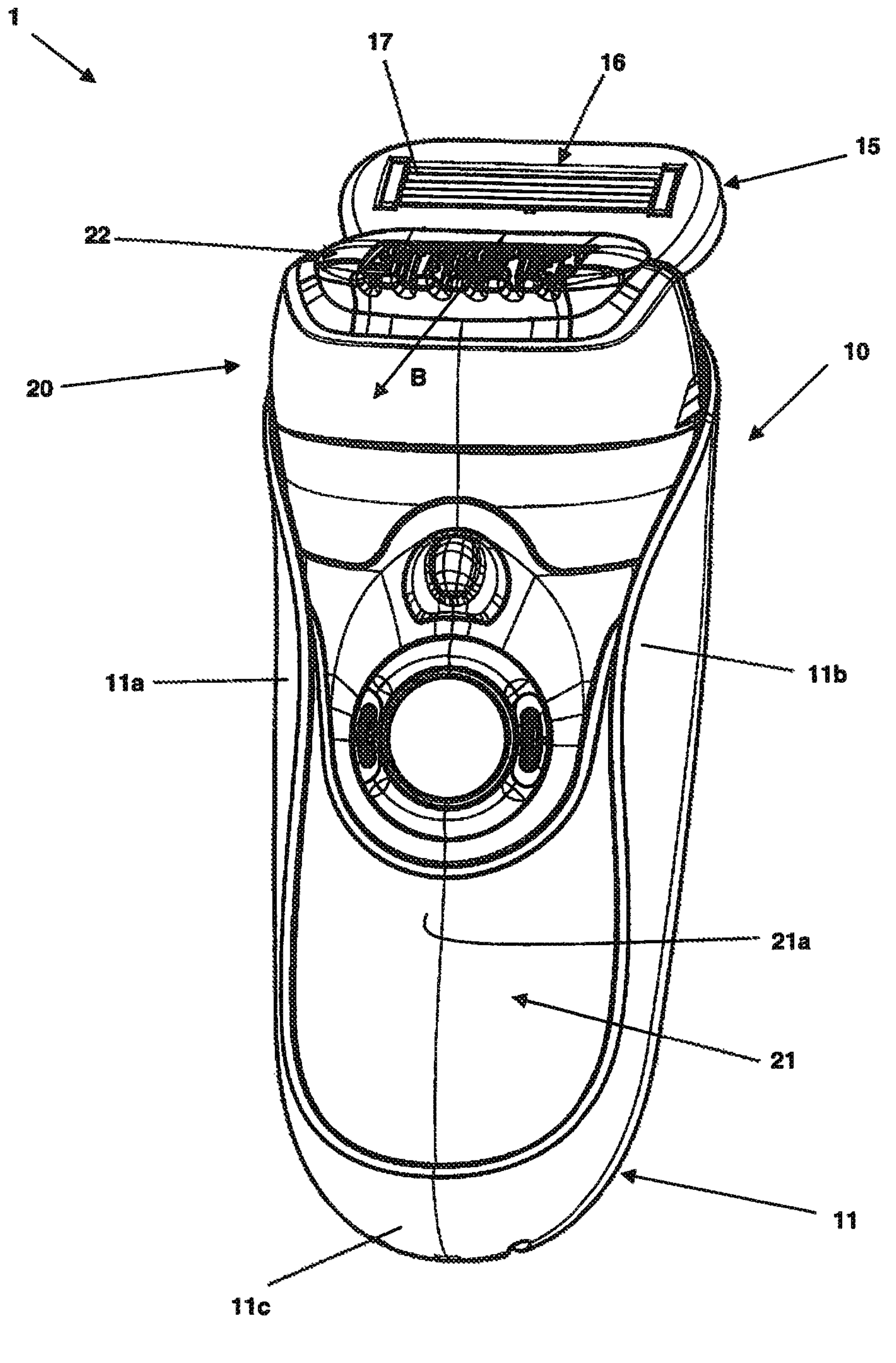
FIG. 3 is a perspective view onto an exemplary hybrid hair removal device as proposed, where an attachment is clamped onto an electrical hair removal device realized as an epilator device.

FIG. 1A is a view onto the front of an exemplary attachment 10 as proposed. The attachment 10 is intended to be detachably slipped over a body of an electrical hair removal device so as to form a hybrid hair removal device. In the attached state, the handle structure envelopes at least a part of the body. The attachment 10 therefore comprises a handle structure 11 that in the shown embodiment will be clamped around a body of the electrical hair removal device (the resulting hybrid hair removal device is shown in FIG. 3). Insofar, the attachment 10 does not require any modification of an available electrical hair removal device. A user can simply slip the attachment 10 over the electrical hair removal device as one would slip a shoe over a foot. The attachment 10 further comprises a skin treatment unit 15 that in the shown embodiment is realized as a safety razor cartridge that comprises a blade block 16 in which several razor blades 17 are mounted as is generally known from a safety razor such as the Gillette Venus® Embrace. The skin treatment unit 15 may generally be realized as any kind of skin treatment device such as a massaging roller, an applicator for applying an application material (e.g. via a lubrication strip or via a sponge etc.), a razor blade or several razor blades for shaving off hairs from the skin etc. The skin treatment to unit 15 may also comprise several of the mentioned treatment units. E.g. the skin treatment unit 15 as shown may further comprise a lubrication strip and/or massaging lamellae. Different attachments 10 may be provided to enable the user to add different additional functions to an electrical hair removal device in a simple and fast manner.

The handle structure 11 is preformed so as to tightly fit around the body of the electrical hair removal device for which it is intended. The handle structure 11 has an inner side 12 that is shaped to accommodate the body of the electrical hair removal device. The handle structure 11 has flexed parts 11*a*, 11*b*, and 11*c* that will be clamped around the body of the electrical hair removal device. In the shown example, the flexed parts 11*a*, 11*b*, and 11*c* extend on three sides of the handle structure 11 (namely left side, right side and bottom side with reference to the paper direction). The flexed parts 11*a*, 11*b*, and 11*c* are bent inwards so as to partially embrace the hollow space formed by the concave inner side 12 of the handle structure so that the handle structure 11 can be clamped around three sides of the body of the electrical hair removal device. Instead of three sides, the handle structure 11 may have only two flexed parts 11*a* and 11*b* and the handle structure 11 would then only be clamped around two sides of the body of the electrical hair removal device. In another embodiment, the handle structure may have further flexed parts at the top, e.g. short flexed straps left and right of the skin treatment unit 15 that will be clamped around a head part of the body of the electrical hair removal device. At least the flexed parts 11*a* and 11*b* are preformed such that they are bent slightly outwards when the handle structure 11 is slipped over the body of the electrical hair removal device. Due to clamping forces applied via the bent flexed parts 11*a* and 11*b* (and optionally 11*c*) the attachment 10 is fixedly connected with the electrical hair removal device. By a specific choice of the material of the handle structure 11 and/or a coating of the inner surface 12*a* of the handle structure 11 and/or a certain roughness of the inner surface 12*a* of the handle structure 11, the fixation can be enhanced due to adhesion and friction resistance between the inner surface 12*a* of the handle structure 11 and the outer surface of the body of the electrical hair removal device.

Figure 1B:
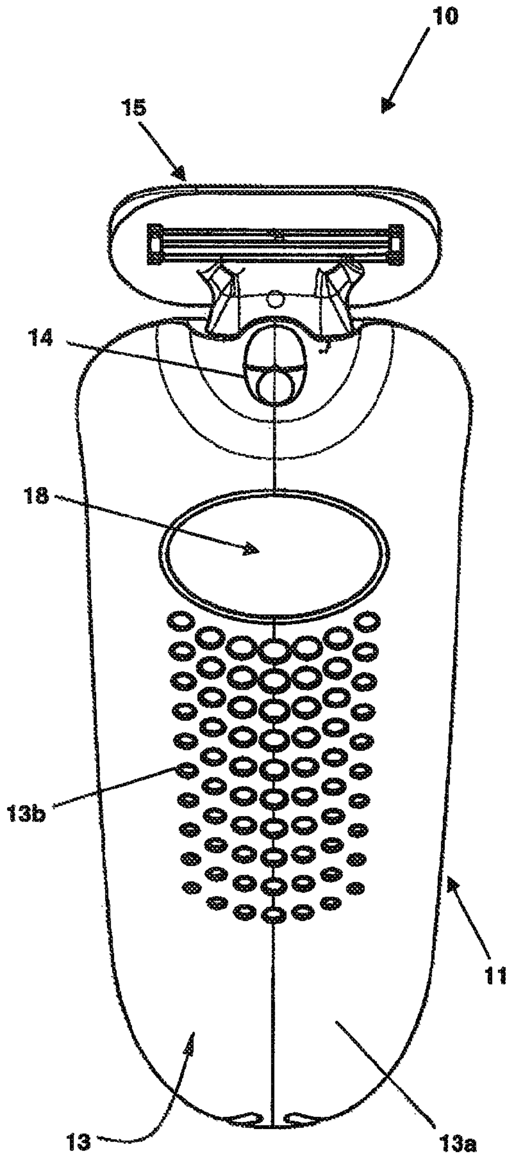
FIG. 1B is a view onto the back side of the attachment as shown in FIG. 1A.

FIG. 1B is a view onto the back of the attachment 10 as depicted in FIG. 1A. The handle structure 11 comprises a release mechanism 14 as is known from safety razors to release the skin treatment unit 15 from a clamp structure that holds the skin treatment unit 15. Obviously, the shown release mechanism 14 is just one exemplary embodiment of a release mechanism that could be employed. The skin treatment unit 15 may also be floatingly mounted to the handle structure, e.g. by to mounting the skin treatment unit 15 onto a guided spring that allows for a vertical floating motion of the skin treatment unit 15 under application of a force. Further, the outer side 13 of the handle structure 11 that is intended to be gripped by a user's hand during operation is visible. The outer side 13 has an outer surface 13*a* and has a texture 13*b*, that in the shown case is realized as a perforation of a part of the outer surface 13*a*. The texture 13*b* enhances the grip of the handle structure 11, specifically when used in a wet environment, e.g. under the shower. Instead of perforations, the texture could be realized as depressions or elevations (e.g. rips, burls etc.). The enhancement of the grip, specifically in a wet environment, is optimal if the texture has a macroscopic size, i.e. when at least a lateral dimension of the texture elements has a minimal value such as 0.5 mm or 1 mm or 2 mm or 5 mm.

The handle structure 11 further has an opening 18 that is shaped so as to form-fit around a projecting part of the body of the electrical hair removal part. Such a form-fit connector element enhances the fixed connection between handle structure 11 and body of the electrical hair removal device. In general, the handle structure 11 could comprise a first connector structure that mates with a second connector structure realized at the body of the electrical hair removal device, e.g. the handle structure 11 could comprise elastic, mush-room-like projections and the body could comprises undercut cavities that receive the mush-room-like projections in a releasable snap-fit manner.

Figure 2:
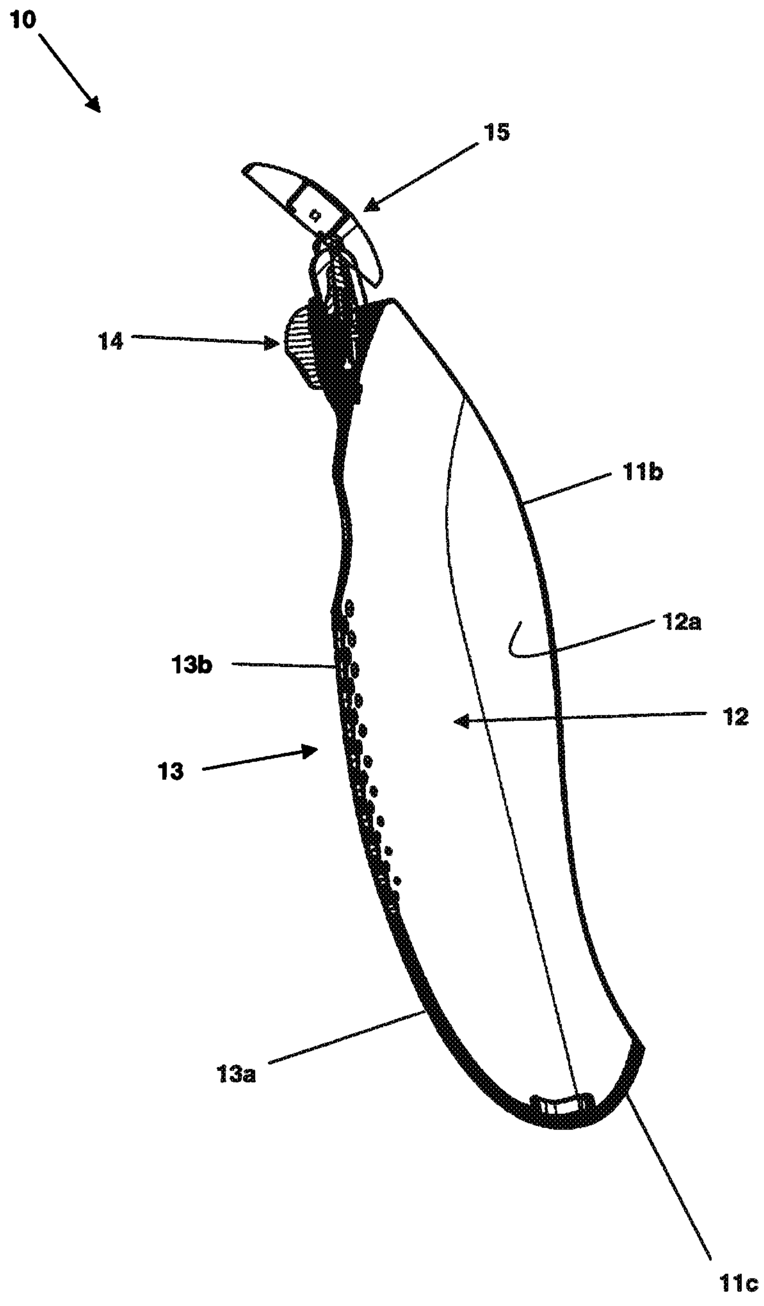
FIG. 2 is a cross sectional cut through the attachment as shown in FIGS. 1A and 1B along the line A-A as indicated in FIG. 1A.

FIG. 2 shows a cross sectional cut through the attachment 10 as depicted in FIGS. 1A and 1B along line A-A as indicated in FIG. 1A. The handle structure 11 has a relatively thin wall thickness, typically in the range of 0.5-3 mm The inner side 12 of the handle structure 11 is shaped to accommodate the body of the electrical hair removal device. Flexed parts 11*b* and 11*c* are bent inwards to partially embrace the hollow space defined by the inner side 12 of the handle structure 11. The clamp structure and the release button of the release mechanism 14 are visible.

FIG. 3 is a perspective view of a hybrid hair removal device 1 where the attachment 10 as shown in FIGS. 1A, 1B, and 2 is clamped around an electrical hair removal device 20, which in the shown embodiment is realized as an epilator device. The electrical hair removal device 20 has a body 21 that is intended to be gripped by a user's hand when the attachment 10 is detached. The electrical hair removal device 20 further has a head 22 that is intended to get in contact with a user's skin to remove hairs. The handle structure 11 of the attachment 10 is clamped around the electrical hair removal device 20 in such a way that the head 22 remains uncovered by the handle structure 11. The skin treatment unit 15 is arranged at the attachment 10 in such a way that the razor blade 17 lies behind the head 22 with respect to a use direction B defined by the cutting edge of the razor blade as the blade will only cut hairs when drawn over the skin along the use direction B. Hence, the hybrid hair removal device 1 as shown will completely remove hairs in a single stroke. Firstly, hairs growing on the skin are plucked out by the head 22 realized as an epilation cylinder and secondly the remaining hairs that were not plucked out are cut off by the skin treatment unit 15 that is realized as a safety razor head. Since the flexed parts 11*a*, 11*b*, and 11*c* partially embrace a hollow space formed by the inner side 12 of the handle structure 11 that is slightly smaller than the body 21 of the electrical hair removal device 20, the flexed parts 11*a*, 11*b*, and 11*c* are pre-stressed against the body 21 and thus the handle structure 11 is fixed to the body 21 of the electrical hair removal device 20.

European patent application No. 08012724.4 describes a combined shaving device that comprises a first shaving device, in particular an electric dry shaving device such as a trimmer, having a first connector structure and a second shaving device, in particular a wet shaving device comprising a shaving head with at least a razor blade having a sharp edge, having a second connector structure, where the first and second connector structures detachably mate with each other, and the first and second shaving device each having an elongated handle for individual use of the first and second shaving device in a detached state. In extension of this invention, a hybrid epilator device could be formed in which the first shaving device is replaced by an epilator device. In such a case, the elongated handle needs not to envelope the body of the epilator device as was described above as the first and second connector structures establish the detachable connection.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm. "

What is claimed is:

1. Hybrid hair removal device comprising:

an electrical epilator comprising a body that is intended for being gripped by a user's hand and a head that is in contact with a user's skin during regular operation; and an attachment that comprises:

a handle structure that detachably envelopes at least a part of the outer surface of the body, said handle structure having an outer side that is at least partially textured for gripping by a user's hand and, a skin treatment unit detachably connected to the handle structure, said skin treatment unit comprising at least a razor blade floatingly mounted on the handle structure so that the epilator and the blade simultaneously contact the skin, and wherein the epilator lies in front of the blade with respect to the use direction of the device.

2. Hybrid hair removal device according to claim 1, wherein the skin treatment unit comprises a safety razor unit that comprises the razor blade.

3. Hybrid hair removal device according to claim 1, wherein the handle structure comprises a release mechanism to detach the skin treatment unit from the handle structure.

4. Hybrid hair removal device according to claim 3, wherein the skin treatment unit is floatingly connected to the handle structure.

5. Hybrid hair removal device according to claim 4, wherein the attachment of the skin treatment unit comprises a fixation mechanism for fixing the skin treatment unit with respect to the handle structure.

6. Hybrid hair removal device according to claim 5 wherein the handle structure envelopes two sides of the body.

7. Hybrid hair removal device according to claim 6, wherein the handle structure envelopes three sides of body.

8. Hybrid hair removal device according to claim 7, wherein the handle structure comprises a first connector structure that mates with a second connector structure on the body.

9. Hybrid hair removal device according to claim 1, wherein the outer side of the handle structure is at least partially equipped with depressions or elevations that constitute the texture.

* * * * *